(12) United States Patent
Kagara et al.

(10) Patent No.: US 6,355,800 B1
(45) Date of Patent: Mar. 12, 2002

(54) PROCESS FOR PRODUCING AMINOPIPERAZINE DERIVATIVES

(75) Inventors: Kooji Kagara, Mino; Norio Hashimoto, Ibaraki; Atsushi Kanda; Yukihisa Baba, both of Nishinomiya; Tetsuo Furutera, Takarazuka, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/509,812

(22) PCT Filed: Sep. 28, 1998

(86) PCT No.: PCT/JP98/04352

§ 371 Date: Apr. 6, 2000

§ 102(e) Date: Apr. 6, 2000

(87) PCT Pub. No.: WO99/19315

PCT Pub. Date: Apr. 22, 1999

(30) Foreign Application Priority Data

Oct. 9, 1997 (JP) .............................. 9-293478

(51) Int. Cl.$^7$ ..................... C07D 295/32; C07D 409/06
(52) U.S. Cl. ...................... 544/379; 544/382
(58) Field of Search ................. 544/382, 379

(56) References Cited

U.S. PATENT DOCUMENTS

| | | | | |
|---|---|---|---|---|
| 4,797,399 A | * | 1/1989 | Ueda et al. ................ | 514/253 |
| 5,250,528 A | * | 10/1993 | Oku et al. .................. | 514/252 |
| 5,708,172 A | * | 1/1998 | Oku et al. .................. | 544/382 |
| 6,147,079 A | * | 11/2000 | Kitamura et al. ...... | 514/255.01 |
| 6,291,464 B1 | * | 9/2001 | Shima et al. .......... | 514/255.01 |

FOREIGN PATENT DOCUMENTS

| | | |
|---|---|---|
| GB | 2 162 843 | 2/1986 |
| JP | 39-19175 | 9/1964 |
| WO | WO 91/01979 | 2/1991 |
| WO | WO 95/00502 | 1/1995 |

* cited by examiner

*Primary Examiner*—Emily Bernhardt
(74) *Attorney, Agent, or Firm*—Oblon, Spivak, McClelland, Maier & Neustadt, P.C.

(57) ABSTRACT

A new industrial process excellent in yield and purity for preparing a compound of the formula:

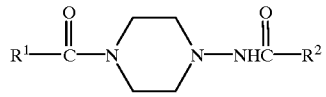

or a salt thereof in a less number of steps with a synthetic pathway without proceeding via nitroso compounds, wherein $R^1$ is lower aryl, ar(lower)alkoxy or heterocyclic group, each of which may be substituted with halogen, and $R^2$ is cyclo(lower)alkyl, aryl or ar(lower)alkyl, each of which may be substituted with halogen.

2 Claims, No Drawings

PROCESS FOR PRODUCING AMINOPIPERAZINE DERIVATIVES

TECHNICAL FIELD

The present invention relates to a new industrial process excellent in yield and purity for producing aminopiperazine derivatives and pharmaceutically acceptable salts thereof in a less number of steps with a synthetic pathway without proceeding via nitroso compounds, and is useful in a pharmaceutical field.

BACKGROUND TECHNOLOGY AND PROBLEM

The process for preparing aminopiperazine derivatives of the present invention is described in an international patent application (international publication number WO91/01979) published based on the Patent Cooperation Treaty. By the said process, however, isolation and purification of intermediate products are not necessarily easy owing to water-solubility thereof or the like, so mass production of the aminopiperzine derivatives was difficult.

Additionally, the process for preparing aminopiperazine derivatives of the present invention is described in an international patent application (international publication number WO95/00502) published based on the Patent Cooperation Treaty. However, said process had many problems as an industrial synthetic process because of a large number of steps (6 steps), use of a large amount of methylene chloride as a solvent for extraction, occurrence of carcinogenic nitroso compounds as intermediates, and the necessity for reduction reaction with metallic zinc.

CONSTITUTION OF INVENTION

One object of the present invention is to provide new processes for preparing the aminopiperazine derivatives and pharmaceutically acceptable salts thereof which possess the potentiation of the cholinergic activity and are useful for treating disorders in the central nervous system, especially for treating amnesia, dementia, senile dementia, and the like in human being.

According to the present invention, the aminopiperazine derivatives of the object compound (I) or pharmaceutically acceptable salts thereof can be prepared by the following processes.

Process 1

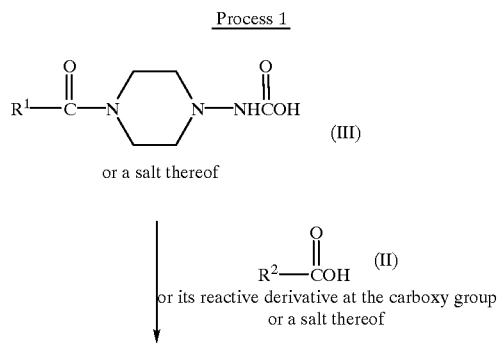

or a salt thereof

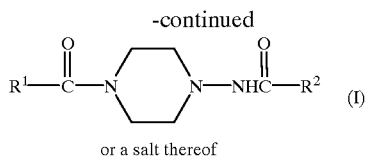

or a salt thereof wherein $R^1$ is lower alkyl, aryl, ar(lower)alkoxy or heterocyclic group, each of which may be substituted with halogen, and $R^2$ is cyclo(lower)alkyl, aryl or ar(lower)alkyl, each of which may be substituted with halogen.

Process 2

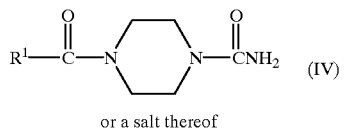

or a salt thereof step 1: hypochlorite or hypobromite
step 2:

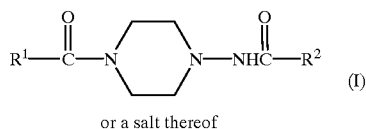

or its reactive derivative at the carboxy group
or a salt thereof wherein $R^1$ is lower alkyl, aryl, ar(lower)alkoxy or heterocyclic group, each of which may be substituted with halogen, and $R^2$ is cyclo(lower)alkyl, aryl or ar(lower)alkyl, each of which may be substituted with halogen.

In the above and subsequent descriptions of the present specification, suitable examples of the various definitions to be included within the scope of the invention are explained in detail as follows.

The term "lower" is intended to mean 1 to 6 carbon atom(s), unless otherwise indicated.

Suitable "lower alkyl" may include a straight or branched one such as methyl, ethyl, propyl, isopropyl, butyl, isobutyl, t-butyl, pentyl, hexyl, and the like, in which the preferable one is methyl.

Suitable "aryl" may include phenyl, naphthyl, tolyl, xylyl, mesityl, cumenyl, and the like, in which the preferable one is phenyl or naphthyl.

Suitable "ar(lower)alkoxy" may include benzyloxy, phenethyloxy, phenylpropoxy, benzhydryloxy, trityloxy, and the like.

Suitable "heterocyclic group" may include saturated or unsaturated monocyclic group containing at least one hetero-atom such as nitrogen, oxygen and sulfur atom.

Preferable "heterocyclic group" thus defined may be unsaturated 3 to 8-membered (more preferably 5 or 6-membered) heteromonocyclic group containing 1 to 4 nitrogen atom(s), for example, pyrrolyl, imidazolyl, pyrazolyl, pyridyl, pyridyl N-oxide, dihydropyridyl, tetrahydropyridyl, pyrimidyl, pyrazinyl, pyridazinyl, triazinyl, triazolyl, tetrazinyl, tetrazolyl, etc.;

unsaturated condensed heterocyclic group containing 1 to 5 nitrogen atom(s), for example, idolyl, isoindolyl, indolizinyl, benzimidazolyl, quinolyl, isoquinolyl, indazolyl, benzotriazolyl, etc.;

unsaturated 3 to 8-membered heteromonocyclic group containing 1 to 2 oxygen atom(s) and 1 to 3 nitrogen atom(s), for example, oxazolyl, isoxazolyl, oxadiazolyl, etc.;

saturated 3 to 8-membered heteromonocyclic group containing 1 to 2 oxygen atom(s) and 1 to 3 nitrogen atom(s), for example, morpholino, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered heteromonocyclic group containing 1 to 2 sulfur atom(s) and 1 to 3 nitrogen atom(s), for example, thiazolyl, isothiazolyl, thiadiazolyl, etc.;

unsaturated 3 to 8-membered heteromonocyclic group containing 1 to 2 sulfur atom(s), for example, thienyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered heteromonocyclic group containing an oxygen atom, for example, furyl, etc.;

unsaturated condensed heterocyclic group containing 1 to 2 sulfur atom(s), for example, benzothienyl, etc.;

unsaturated condensed heterocyclic group containing 1 to 2 oxygen atom(s), for example, benzofuranyl, etc., and the like.

Suitable "cyclo(lower)alkyl" may include cyclopropyl, cyclobutyl, cyclopentyl, cyclohexyl, and the like.

Suitable "ar(lower)alkyl" may include benzyl, phenethyl, phenylpropyl, benzhydryl, trityl, and the like.

"Lower alkyl", "aryl", "ar(lower)alkoxy", "heterocyclic group", "cyclo(lower)alkyl" and "ar(lower)alkyl" described above may be substituted with halogen [e.g. fluoro, chloro, bromo and iodo].

Pharmaceutically acceptable salts of the object compound (I) are conventional non-toxic salts and may include an acid addition salt such as an inorganic acid addition salt (e.g. hydrochloride, hydrobromide, sulfate, phosphate, etc.), an organic acid addition salt (e.g. formate, acetate, trifluoroacetate, maleate, tartrate, methanesulfonate, benzenesulfonate, toluensulfonate etc.); a salt with an amino acid (e.g. aspartic acid salt, glutamic acid salt, etc.); and the like.

The processes for preparing the object compound(I) are explained in detail in the following.

PROCESS 1

The compound(I) or a salt thereof can be prepared by reacting the compound(III) or a salt thereof with the compound(II) or its reactive derivative at the carboxy group or a salt thereof.

Suitable salts of the compound(III) can be reffered to the ones as exemplified for the compound(I).

Suitable reactive derivative at the carboxy group of the compound (II) may include an ester, an acid halide, an acid anhydride, and the like. Suitable examples of the reactive derivatives may be an acid halide (e.g. acid chloride, acid bromide, etc.); a symmetrical acid anhydride; a mixed acid anhydride with an acid such as aliphatic carboxylic acid (e.g. acetic acid, pivalic acid, etc.), substituted phosphoric acid (e.g. dialkylphosphoric acid, diphenylphosphoric acid, etc.); an ester such as substituted or unsubstituted lower alkyl ester (e.g. methyl ester, ethyl ester, propyl ester, hexyl ester, trichloromethyl ester, etc.), substituted or unsubstituted ar(lower)alkyl ester (e.g.benzyl ester, benzhydryl ester, p-chlorobenzyl ester, etc.), substituted or unsubstituted aryl ester (e.g. phenyl ester, tolyl ester, 4-nitrophenyl ester, 2,4-dinitrophenyl ester, pentachlorophenyl ester, naphtyl ester, etc.), or an ester with N,N-dimethylhydroxylamine, N-hydroxysuccinimide, N-hydroxyphthalimide or 1-hydroxy-6-chloro-1H-benzotriazole. These reactive derivatives can optionally be selected from them according to the kind of the compound (II) to be used.

In this reaction, compound (III) or a salt thereof is reacted with compound (II) or a reactive derivative at the carboxy group or a salt thereof, to form a mixed acid anhydride of compounds (III) and (II), which is then is decarbonated to form compound (I).

In this reaction, however, compound (III) may be decarbonated depending on reaction conditions to form the following compound:

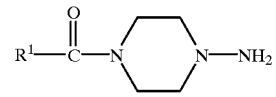

, with which compound (II) or a reactive derivative at the carboxy group or a salt thereof reacts, thus giving compound (I). This reaction is also encompassed by the process of this invention.

The process is carried out in a conventional solvent such as dioxane, chloroform, methylene chloride, tetrahydrofuran or any other conventional solvent which does not adversely influence the reaction.

When the compound (II) is used in a free acid form or its salt form in the reaction, the reaction is preferably carried out in the presence of a conventional condensing agent such as N,N'-dicyclohexylcarbodiimide, N-cyclohexyl-N'-morpholinoethylcarbodiimide, N-ethyl-N'-(3-dimethylaminopropyl)carbodiimide, thionyl chloride, oxalyl chloride, lower alkoxycarbonyl halide (e.g. ethyl chloroformate, isobutyl chloformate, etc.), 1-(p-chlorobenzenesulfonyloxy)-6-chloro-1H-benzotriazole, or the like.

The reaction temperature is not critical and the reaction is usually carried out at ambient temperature or under heating.

PROCESS 2

In this reaction, compound (IV) or a salt thereof is reacted in step 1 with hypochlorite or hypobromite to form the following compound:

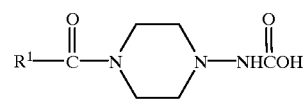

or a salt thereof or the following compound:

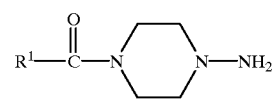

or a salt thereof, and this product may be isolated and then reacted in step 2 with compound (II) or a reactive derivative at the carboxy group or with a salt thereof, to give compound (I) or a salt thereof, or said product may, without being isolated, be reacted with compound (II) or a reactive derivative at the carboxy group or with a salt thereof. Each case is encompassed by the process of the present invention.

Preferable examples of hypochlorite and hypobromite include a salt with alkali metal (sodium, potassium, etc.) or with alkaline earth metal (calcium etc.).

Because step 1 proceeds in a known reaction form as Hofmann rearrangement, the reaction reagents and reaction conditions (e.g., solvent, reaction temperature, etc.) include those known to cause the Hofmann rearrangement.

Suitable reaction solvent in the reaction of step 1 is water. The reaction temperature is not critical and the reaction is preferably carried out at ambient temperature or under heating.

The reaction of step 2 can be carried out in substantially the same manner as above process 1, therefore reaction reagent and reaction condition (e.g. solvent, reaction temperature, etc.) described in process 1 may be used.

The compounds obtained by the above processes can be isolated and purified by a conventional method such as pulverization, recrystallization, column chromatography, reprecipitation, or the like.

The compound (I) and other compounds may include more than one optical isomer due to asymmetric carbon atom(s). The isomer and mixture thereof may be included in the scope of the invention.

Further, the hydrate of compound (I) may be included in the scope of the invention.

The object compound (I) and pharmaceutically acceptable salts thereof possess a strong potentiation of the cholinergic activity and they are useful for treating disorders in the central nervous system, especially for treating amnesia, dementia, senile dementia, and the like in human being.

One object of the present invention is to provide the new processes for preparing the compound (I) or a salt thereof as described above.

The present invention is based on finding that the processes for preparing the object compound (I) and sals thereof are superior to the known processes in point of yield and purity, and further in point of a less number of steps with a synthetic pathway without proceeding via nitroso compounds.

The following Preparations and Examples are given for the purpose of illustrating the present invention in more detail, and don't restrict the scope of the invention.

PREPARATION 1

N-Acetylpiperazine (25.0 g) was added to water (100 ml) and dissolved under stirring at ambient temperature. Then, the solution was adjusted to pH 3.0 with 6 N hydrochloric acid (about 33 ml). After the solution was cooled, sodium isocyanate (15.2 g) was added in one portion thereto at a temperature of 5 to 10° C. Thereafter, the mixture was reacted for 4 hours at ambient temperature and then cooled on ice to −2 to 2° C. The mixture was stirred at the same temperature for 2 hours to precipitate 4-acetyl-1-piperazinecarboxamide crystals. The crystals were collected at the same temperature by filtration, washed with cold water (25 ml) and dried under reduced pressure to give primary crystals of 4-acetyl-1-piperazinecarboxamide (17.7 g). The mother liquor containing the primary crystals was concentrated to 63 ml under reduced pressure and then stirred at −2 to 2° C. for 2 hours to precipitate secondary crystals of 4-acetyl-1-pipeazinecarboxamide. The crystals were collected at the same temperature by filtration, washed with cold water (13 ml) and dried under reduced pressure to give secondary crystals of 4-acetyl-1-piperazinecarboxamide (9.3 g). NMR (DMSO-d6, δ): 2.00 (3H, s), 3.21–3.41 (8H, m), 6.04 (2H, Broad s)

EXAMPLE 1

1 N Aqueous sodium hydroxide (70 ml) and water (30 ml) were cooled at 5 to 10° C., and 4-acetyl-1-piperazinecarboxamide (10.0 g) was added thereto and dissolved under stirring. 10% Aqueous sodium hypochlorite (43.5 ml) was added in one portion thereto at the same temperature and allowed to react for 1 hour at the same temperature, and after the temperature was raised, the mixture was further reacted for 2 hours at a temperature of 15 to 20° C. The reaction solution containing 4-acetyl-1-piperazinylcarbamic acid was adjusted to pH 6.5–7.5 with 1 N hydrochloric acid (about 23 ml), followed by adding tetrahydrofuran (100 ml). A solution of 4-fluorobenzoyl chloride (11.1 g) in tetrahydrofuran (20 ml) was added dropwise thereto at 20 to 30° C. over the period of 1 hour. Because the pH was decreased during the addition, the reaction solution was kept at pH 6.0 to 7.0 with 1 N aqueous sodium hydroxide. After this dropwise addition was finished, the solution was further reacted for 2 hours at the same temperature and at the same pH. The reaction solution was concentrated to 50 ml under reduced pressure, then cooled on ice and stirred at 5 to 10° C. for 1 hour to precipitate N-(4-acetyl-1-piperazinyl)-4-fluorobenzamide. The resultant crystals were collected at the same temperature by filtration, washed with cold water (50 ml) and dried under reduced pressure to give N-(4-acetyl-1-piperazinyl)-4-fluorobenzamide (8.35 g). NMR (DMSO-d6, δ): 2.03 (3H, s), 2.77–2.92 (4H, m), 3.50–3.52 (4H, m), 7.23–7.34 (2H, m), 7.82–7.89 (2H, m), 9.58 (1H, s)

What is claimed is:

1. A process for the preparation of a compound of the formula:

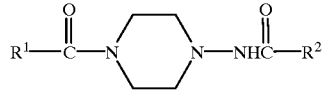

or a salt thereof which comprises reacting a compound of the formula:

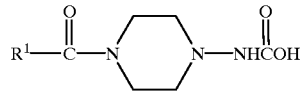

or a salt thereof with a compound of the formula:

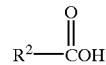

or its reactive derivative at the carboxy group or a salt thereof, wherein $R^1$ is lower alkyl, aryl, ar(lower)alkoxy or a thienyl group, each of which may be substituted with halogen, and $R^2$ is cyclo(lower)alkyl, aryl or ar(lower)alkyl, each of which may be substituted with halogen.

2. A process for the preparation of a compound of the formula:

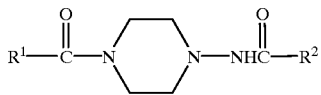

or a salt thereof which comprises reacting a compound of the formula:

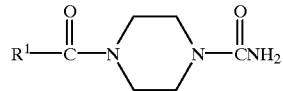

or a salt thereof with a hypochlorite or a hypobromite and then reacting the compound obtained or a salt thereof with a compound of the formula:

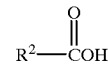

or its reactive derivative at the carboxy group or a salt thereof, wherein $R^1$ is lower alkyl, aryl, ar(lower)alkoxy or a thienyl group, each of which may be substituted with halogen, and $R^2$ is cyclo(lower)alkyl, aryl or ar(lower)alkyl, each of which may be substituted with halogen.

* * * * *